United States Patent
Nzeribe

(10) Patent No.: US 8,841,131 B1
(45) Date of Patent: Sep. 23, 2014

(54) CHOLESTEROL MEASURING APPARATUS AND ASSOCIATED USE THEREOF

(71) Applicant: Ifeanyi Nzeribe, Amityville, NY (US)

(72) Inventor: Ifeanyi Nzeribe, Amityville, NY (US)

(*) Notice: Subject to any disclaimer, the term of this patent is extended or adjusted under 35 U.S.C. 154(b) by 0 days.

(21) Appl. No.: 13/648,240

(22) Filed: Oct. 9, 2012

(51) Int. Cl.
*G01N 33/92* (2006.01)
*G01N 21/78* (2006.01)

(52) U.S. Cl.
USPC ........ 436/71; 436/63; 436/164; 436/165; 436/169; 422/400; 422/402; 422/420; 422/425; 435/11

(58) Field of Classification Search
USPC ............ 436/63, 71, 164, 165, 169, 174; 422/400, 401, 402, 403, 404, 420, 425, 422/430, 68.1, 82.05, 82.09; 435/11, 29
See application file for complete search history.

(56) References Cited

U.S. PATENT DOCUMENTS

| | | | |
|---|---|---|---|
| 4,680,259 A * | 7/1987 | Cumbo et al. | 435/11 |
| 6,078,829 A | 6/2000 | Uchida et al. | |
| 6,544,475 B1 * | 4/2003 | Douglas et al. | 422/402 |
| 2005/0143675 A1 | 6/2005 | Neel et al. | |
| 2005/0165622 A1 | 7/2005 | Neel et al. | |
| 2005/0227370 A1 * | 10/2005 | Ramel et al. | 436/514 |
| 2008/0131918 A1 * | 6/2008 | Jones et al. | 435/11 |
| 2008/0159911 A1 * | 7/2008 | Hsu | 422/55 |
| 2010/0311091 A1 * | 12/2010 | Bae et al. | 435/11 |
| 2011/0200498 A1 * | 8/2011 | Huffstodt | 422/401 |

* cited by examiner

*Primary Examiner* — Maureen Wallenhorst

(57) ABSTRACT

A cholesterol-level measuring apparatus including a portable body having a cholesterol level detecting means for identifying a cholesterol level in a blood sample, and a display screen communicatively coupled to the cholesterol level detecting means for illustrating a learned cholesterol level in the blood sample. Notably, the cholesterol level detecting means includes a disposable test strip having a color-changing reactive reagent that changes color in response to the learned cholesterol level in the blood sample.

7 Claims, 3 Drawing Sheets

US 8,841,131 B1

CHOLESTEROL MEASURING APPARATUS AND ASSOCIATED USE THEREOF

CROSS REFERENCE TO RELATED APPLICATIONS

This application claims the benefit of U.S. Provisional Application No. 61/544,483 filed Oct. 7, 2011, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

1. Technical Field

This non-limiting exemplary embodiment(s) relates to home-test healthcare products and, more particularly, to a cholesterol measuring apparatus for providing users with an easy and convenient means of testing and monitoring cholesterol levels at home.

2. Prior Art

According to the American Heart Association, high cholesterol is one of the major controllable risk factors for coronary heart disease, heart attack, and stroke. In other words, as blood cholesterol rises, so does the risk of coronary heart disease. When too much low-density lipoprotein (LDL), or "bad" cholesterol, circulates in the blood, it can slowly build up in the inner walls of the arteries that feed the heart and brain. Together with other substances, it can form plaque, a thick, hard deposit that can narrow the arteries and make them less flexible. This condition is known as atherosclerosis. If a clot forms and blocks a narrowed artery, a heart attack or stroke can result. Unfortunately, even though high cholesterol levels are very dangerous, most of the time there are no symptoms.

As such, the American Heart Association recommends that all adults over the age of 20 have their cholesterol levels checked every five years, and more often for those over 45 or who have a family history or other risk factors for high cholesterol.

Accordingly, a need remains for home healthcare product to overcome at least one of the above-noted shortcomings. The non-limiting exemplary embodiment(s) satisfies such a need by providing a cholesterol measuring apparatus that is convenient and easy to use, lightweight yet durable in design, versatile in its applications, and designed for easily and conveniently providing users with an easy and convenient means of testing and monitoring cholesterol levels.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a cholesterol measuring apparatus for providing users with an easy and convenient means of testing and monitoring cholesterol levels. These and other objects, features, and advantages of the non-limiting exemplary embodiment(s) are provided by a cholesterol-level measuring apparatus including a portable body having a cholesterol level detecting means for identifying a cholesterol level in a blood sample, and a display screen communicatively coupled to the cholesterol level detecting means for illustrating a learned cholesterol level in the blood sample. Notably, the cholesterol level detecting means includes a disposable test strip having a color-changing reactive reagent that changes color in response to the learned cholesterol level in the blood sample.

In a non-limiting exemplary embodiment, the color-changing reactive reagent has cholesterol-sensitive properties coated on the test strip.

In a non-limiting exemplary embodiment, the cholesterol level detecting means further includes a color-detecting sensor communicatively coupled to the test strip, the color-determining sensor generating and transmitting a color signal upon learning a changed color of the test strip.

In a non-limiting exemplary embodiment, the cholesterol level detecting means further includes a processor and a memory communicatively coupled thereto. In this manner, in response to receiving the color signal, the processor generates and transmits a control signal that causes a digital output to be displayed on the display screen.

In a non-limiting exemplary embodiment, a voice chip and a speaker are communicatively coupled thereto. Such a voice chip emits an audible signal in response to receiving the control signal.

The present disclosure further includes a method of utilizing a cholesterol-level measuring apparatus. Such a method includes the chronological steps of: providing a portable body including a cholesterol level detecting means for identifying a cholesterol level in a blood sample, and a display screen communicatively coupled to the cholesterol level detecting means for illustrating a learned cholesterol level in the blood sample wherein the cholesterol level detecting means includes a disposable test strip having a color-changing reactive reagent; applying the blood sample to the test strip; and the color-changing reactive reagent changing color in response to the learned cholesterol level in the blood sample.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Figure 1:
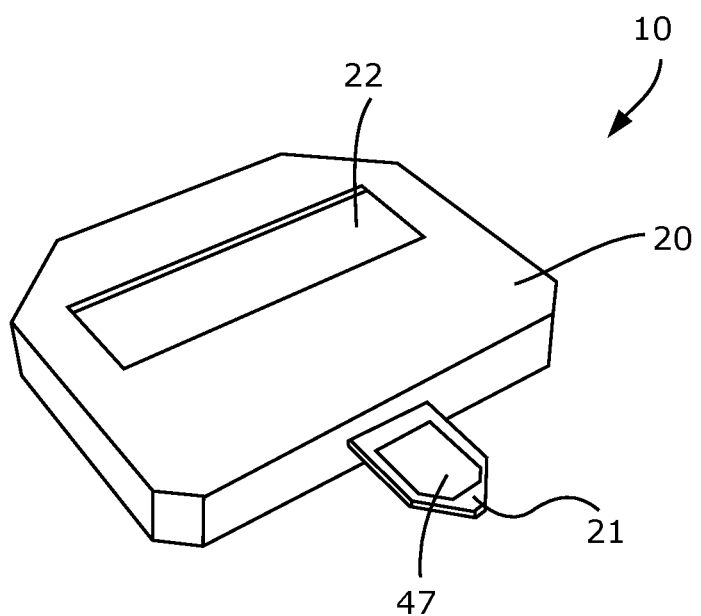
FIG. 1 is a perspective view showing a cholesterol-level determining apparatus, in accordance with the non-limiting exemplary embodiment(s)

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment (s). The appearances of the phrase "non-limiting exemplary emboidment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

Figure 2:
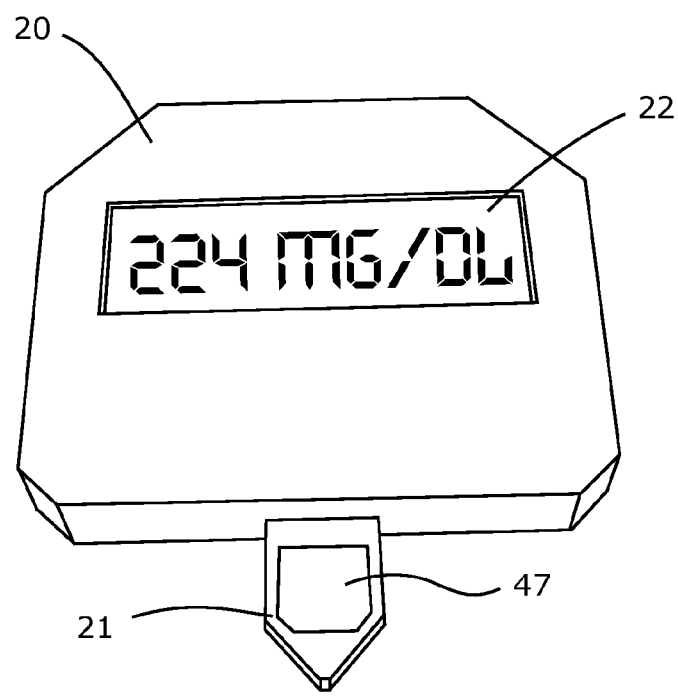
FIG. 2 is a perspective view of the apparatus shown in FIG. 1 wherein a calculated cholesterol level is display on the screen.
Figure 3:
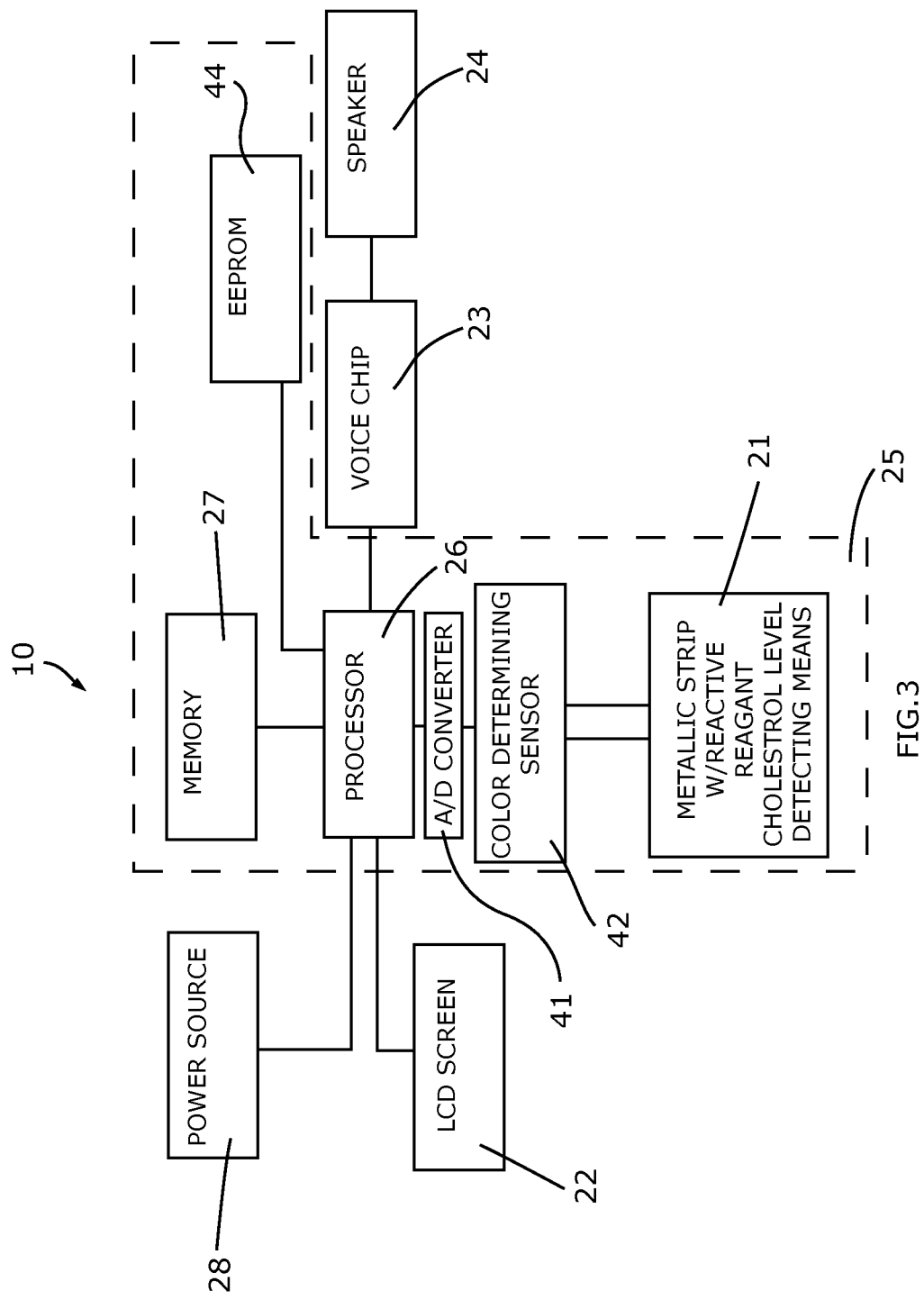
FIG. 3 is a high-level schematic block diagram showing the interrelationship between the major electronic components of the apparatus, in accordance with the non-limiting exemplary embodiment(s).

The non-limiting exemplary embodiment(s) is/are referred to generally in FIGS. 1-3 and is/are intended to provide a cholesterol measuring apparatus 10 for providing users with an easy and convenient means of testing and monitoring cholesterol levels. It should be understood that such non-limiting exemplary embodiment(s) may be used to measure many different types of cholesterol levels, and should not be limited to any specific type of cholesterol.

A cholesterol-level measuring apparatus 10 including a portable body 20 having a cholesterol level detecting means 25 for identifying a cholesterol level in a blood sample, and a display screen 22 communicatively coupled to the cholesterol level detecting means 25 for illustrating a learned cholesterol level in the blood sample. Notably, the cholesterol level detecting means 25 includes a disposable test strip 21 having a color-changing reactive reagent 47 (i.e., test strip 21) that changes color in response to the learned cholesterol level in the blood sample.

In a non-limiting exemplary embodiment, the color-changing reactive reagent 47 has cholesterol-sensitive properties coated on the test strip 21.

In a non-limiting exemplary embodiment, the cholesterol level detecting means 25 further includes a color-detecting sensor 42 communicatively coupled to the test strip 21. Such a color-determining sensor 42 generates and transmits a color signal upon learning a changed color of the test strip 21 (i.e., reactive reagent 47).

In a non-limiting exemplary embodiment, the cholesterol level detecting means 25 further includes a processor 26 and memory 27, 44 communicatively coupled thereto. In this manner, in response to receiving the color signal, the processor 26 generates and transmits a control signal that causes a digital output to be displayed on the display screen 22.

In a non-limiting exemplary embodiment, a voice chip 23 and a speaker 24 are communicatively coupled thereto. Such a voice chip 23 emits an audible signal in response to receiving the control signal from processor 26.

The present disclosure further includes a method of utilizing a cholesterol-level measuring apparatus 10. Such a method includes the chronological steps of: providing a portable body 20 including a cholesterol level detecting means 25 for identifying a cholesterol level in a blood sample, and a display screen 22 communicatively coupled to the cholesterol level detecting means 25 for illustrating a learned cholesterol level in the blood sample wherein the cholesterol level detecting means 25 includes a disposable test strip 21 having a color-changing reactive reagent 47; applying the blood sample to the test strip 21; and the color-changing reactive reagent 47 (i.e., test strip 21) changing color in response to the learned cholesterol level in the blood sample.

Generally, the cholesterol measuring apparatus 10 according to the embodiments of the present disclosure can be used with a large number of types of test elements and test principles. Such test principles are known to the skilled person from the prior art. Thus, for example, optical measuring methods can be used, for example for optical determination of a cholesterol content in blood or urine, which is known for example from DE 698 15 207 T2, which is hereby incorporated herein by reference in its entirety. Alternatively, or in addition, electrochemical test strips 21 can be used, in connection with blood cholesterol concentration measurements and is known for example from U.S. Pat. No. 5,286,362, which is hereby incorporated herein by reference in its entirety.

In a non-limiting exemplary embodiment, the test strip 21 contains a reactive reagent 47 is a film coated thereon follows: first by coating a BIODYNE® B film with organic solvent solution and then drying at an elevated temperature. The second coating, with an aqueous solution, is also followed by drying at elevated temperatures. The BIODYNE® film is coated on the test strip 21 and will now produce a color in proportion to the cholesterol content in blood. The final portion of the strip 21 is a bottom support plate.

In a non-limiting exemplary embodiment, memory 27, 44 such as electrically erasable programmable read only memory 44 (EEPROM) 44 and read only memory 27 (ROM) are provided. Such memory 27, 44 may comprise means 25 other than traditional data storage, such as a "hard-wired" representation of the mathematical relation between reflectance (e.g., color) and constituent (cholesterol) concentration. This memory 27, 44 contains information such as the mathematical relationship between the blood cholesterol level and the current of a photodiode (color sensor 42) which ultimately become a digital value from an analog-to-digital converter 41. Information such as the mathematical characterization would be contained in the nonvolatile memory 27 of the ROM, whereas the EEPROM 44 would contain information that is particular to a single reading such as characterization information for the chemical reactive reagent strip 21 inserted into the body 20 for the cholesterol test. Means for entering characterization values such as through a user interface provides this characterization information to the EEPROM 44 that is necessary for subsequent calculations.

In a non-limiting exemplary embodiment, the digital output of the analog-to-digital converter 41 and information from memory 27, 44 are then provided to a processor 26. The processor 26 is utilized to calculate digitally the blood cholesterol level using characterization information from the EEPROM 44, the mathematical relationship stored in ROM 27 and the light reflectance value (i.e., color change) supplied from the sensor 42 in a digital form by A/D converter 41.

In a non-limiting exemplary embodiment, the processor 26 provides the results of its calculations to a display screen 22 such as liquid crystal display. This allows a presentation in a human understandable form of the calculated concentration of the blood constituent (i.e., HDL/LDL cholesterol) that is measured. In the case of a cholesterol measurement, the output would be in the range of 100-450 milligrams per deciliter.

In a non-limiting exemplary embodiment, when the value measured (adjusted for using the output of different stages of gain) changes less than a predetermined amount in a given period of time the apparatus 10 stores that data as test endpoint data. These values are then used to calculate the level of the blood constituent such as cholesterol. The calculation process may utilize several constants which are characterization parameters of the test strip 21 and are placed into the memory 27, 44 of the apparatus 10. This is accomplished either by scrolling through a display and entering the appropriate values from a menu on the display screen 22 with a user interface or reading the information directly off the test strip 21 and into the memory 27, 44 using a user interface.

In a non-limiting exemplary embodiment, entry of characterization parameters for a given test strip 21, which will be common to any given lot of test strips 21, may be accomplished in a manner well known in the industry. In this way, the characterization parameters of the test strip 21 which constitutes coefficients for the formula used to calculate the end numeral result are entered into the memory 27, 44 of the apparatus 10. Such characterization parameters are well known in the industry.

In a non-limiting exemplary embodiment, when the unit prompts the user to "INSERT STRIP" the user inserts the chemical reagent strip 21. When the unit prompts the user to "ADD BLOOD" the user adds a drop of blood to the test strip 21 which remains inserted in the body 20.

In a non-limiting exemplary embodiment, the measurement block will reflect some light back to a photo detector (i.e., color sensor 42) even if no strip 21 is in place at all. The amount of this reflection (Rblack) can be determined at the factory or immediately prior to each test and then stored to the non-volatile memory 27. Since Rblack voltage is proportional to the intensity of an LED light and since the actual test could be performed at a different light intensity, the Rblack value is calibrated as shown in the following formula: the calibrated Rblack value is subtracted from every measurement to yield true color reflection.

In a non-limiting exemplary embodiment, for the calculation of blood cholesterol level, the formula for calculating the concentration of cholesterol in blood uses several characterization parameters from the test strip 21 and solves a second order equation, well-known by one skilled in the art. After the number is calculated the result is displayed on a liquid crystal display or by other appropriate display.

Error conditions which can be displayed as "TOO LOW" where the result is too low for the device to accurately measure, that is cholesterol is under 100 mg/dl; and "TOO HIGH" where the result is beyond the range of the apparatus 10 that is cholesterol is above 400 mg/dl. In this instance the test is aborted because it would yield inaccurate results. In lower levels of ambient light, however, the resulting ambient light level is subtracted as described above and does not interfere with the test.

In a non-limiting exemplary embodiment, the cholesterol measuring apparatus 10 preferably includes a body 20 made of a lightweight yet durable combination of plastic and metal materials and a strip 21 (e.g., metallic strip) protruding from a side of the body 20. Such a body 20 may be square in shape, measuring approximately 3" in length and width, and 1½" in depth. A voice chip 23 and speaker 24 may further enable the apparatus 10 to provide an audible version of the LDL/HDL results.

The apparatus 10 may further include a liquid crystal display (LCD) screen 22 to visually render one's LDL number, as well as the high-density lipoprotein (HDL), or "good" cholesterol level. The latter number may be important to know since a low HDL reading can be cause for concern, just as a high LDL reading can. The apparatus 10 may include a LDL/HDL detecting means 25 and a processor 26 with a memory 27 communicatively linked to the voice chip 23 and speaker 24. A power source 28 may further be located with the body 20 to power the various components of the apparatus 10.

The processor 26 may be a microprocessor or other devices capable of being programmed or configured to perform computations and instruction processing in accordance with the invention. Such other devices may include microcontrollers, digital signal processors (DSP), Complex Programmable Logic Device (CPLD), Field Programmable Gate Arrays (FPGA), application-specific integrated circuits (ASIC), discrete gate logic, and/or other integrated circuits, hardware or firmware in lieu of or in addition to a microprocessor. Functions and process steps described herein may be performed using programmed computer devices and related hardware, peripherals, equipment and networks. When programmed, the computing devices are configured to perform functions and carry out steps in accordance with principles of the invention. Such programming may comprise operating systems, software applications, software modules, scripts, files, data, digital signal processors (DSP), application-specific integrated circuit (ASIC), discrete gate logic, or other hardware, firmware, or any conventional programmable software, collectively referred to herein as a module.

The memory 27 may include programmable software instructions that are executed by the processor 26. In particular, the programmable software instructions include a plurality of chronological operating steps that define a control logic algorithm for performing the intended functions of the present invention. Such software instructions may be written in a variety of computer program languages such as C++, Fortran and Pascal, for example. One skilled in the art understands that such software instructions may contain various Boolean logic processes that perform the intended function of the present invention. Therefore, the specific source or object code of the software program is not intended to be a limiting factor in executing the present invention's intended function. The memory, which enables storage of data and programs, may include RAM, ROM, flash memory and any other form of readable and writable storage medium known in the art or hereafter developed.

The power source 28 may include one or more rechargeable or non-rechargeable disposable batteries, photovoltaic cells or other power supply means.

There are several significant benefits and advantages associated with the cholesterol measuring apparatus 10. Conceived with health and safety in mind, the apparatus 10 may prove an invaluable tool to anyone concerned with their health and well-being. A home-based monitor for cholesterol levels, the apparatus 10 may allow individuals to test their cholesterol levels in the comforts of their own dwellings, without the need to repeatedly pay for doctor's office visits just to see where their levels are. At the same time, the apparatus 10 may inform both men and women if medical attention is necessary, and then they can begin immediate treatment. The apparatus 10 may help save lives by informing users of bad cholesterol numbers before it is too late.

In use, the cholesterol measuring apparatus 10 would be simple and straightforward to use. A user may simply employ a lancet to draw a drop of blood, which may be placed on the metallic strip 21. The apparatus 10 may then test the blood, and offer the user his or her cholesterol levels. Should the apparatus 10 provide results of elevated LDL (typically over 200 mg/DL) and/or low HDL (less than 40 mg/DL), the user will know for certain that an appointment with a health care professional should be made to begin immediate treatment.

While non-limiting exemplary embodiment(s) has/have been described with respect to certain specific embodiment (s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment (s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed is:

1. A cholesterol-level measuring apparatus comprising:
   a body including
   a cholesterol level detecting means for identifying a cholesterol level in a blood sample; and
   a display screen directly coupled to said cholesterol level detecting means for illustrating a learned cholesterol level in the blood sample;
   wherein said cholesterol level detecting means includes
      a test strip that is metallic and has a color-changing reactive reagent that changes color in response to the learned cholesterol level in the blood sample, wherein said color-changing reactive reagent has cholesterol-sensitive properties coated on said test strip,
      a color-detecting sensor directly coupled to said test strip, said color detecting sensor generating and transmitting a color signal upon learning a changed color of said test strip,
      a processor and a memory directly coupled thereto, and
      an analog-to-digital convertor directly coupled to each said color-detecting sensor and said processor;
   wherein, in response to receiving said color signal, said processor generates and transmits a control signal that causes a digital output to be displayed on said display screen.

2. The cholesterol-level measuring apparatus of claim 1, further comprising: a voice chip and a speaker communicatively coupled thereto; wherein said voice chip emits an audible signal in response to receiving said control signal.

3. A cholesterol-level measuring apparatus comprising:
   a portable body including
   a cholesterol level detecting means for identifying a cholesterol level in a blood sample; and
   a display screen communicatively coupled to said cholesterol level detecting means for illustrating a learned cholesterol level in the blood sample;
   wherein said cholesterol level detecting means includes a disposable test strip having a color-changing reactive reagent that changes color in response to the learned cholesterol level in the blood sample;
   wherein said disposable test strip includes a film comprising a coating of a positively charged nylon membrane with an organic solvent solution and said color-changing reactive reagent.

4. The cholesterol-level measuring apparatus of claim 3, wherein said color-changing reactive reagent has cholesterol-sensitive properties coated on said test strip.

5. The cholesterol-level measuring apparatus of claim 4, wherein said cholesterol level detecting means further comprises: a color-detecting sensor communicatively coupled to said test strip, said color-detecting sensor generating and transmitting a color signal upon learning a changed color of said test strip.

6. The cholesterol-level measuring apparatus of claim 5, wherein said cholesterol level detecting means further comprises: a processor and a memory communicatively coupled thereto;

wherein, in response to receiving said color signal, said processor generates and transmits a control signal that causes a digital output to be displayed on said display screen.

7. The cholesterol-level measuring apparatus of claim 6, further comprising: a voice chip and a speaker communicatively coupled thereto; wherein said voice chip emits an audible signal in response to receiving said control signal.

\* \* \* \* \*